United States Patent [19]
Ohara et al.

[11] Patent Number: 5,770,682
[45] Date of Patent: Jun. 23, 1998

[54] METHOD FOR PRODUCING POLYLACTIC ACID

[75] Inventors: Hitomi Ohara, Kyoto; Seiji Sawa, Ohtsu; Masahiro Ito; Yasuhiro Fujii, both of Kyoto; Masaaki Oota, Mukou; Hideshi Yamaguchi, Chohu, all of Japan

[73] Assignee: Shimadzu Corporation, Kyoto, Japan

[21] Appl. No.: 678,328

[22] Filed: Jul. 11, 1996

[30]     Foreign Application Priority Data

| Jul. 25, 1995 | [JP] | Japan | 7-188796 |
| Nov. 30, 1995 | [JP] | Japan | 7-312180 |
| Nov. 30, 1995 | [JP] | Japan | 7-312181 |
| Nov. 30, 1995 | [JP] | Japan | 7-312182 |

[51] Int. Cl.$^6$ .................................................. C08G 63/08
[52] U.S. Cl. ........................ 528/354; 528/357; 528/361
[58] Field of Search ................................. 528/354, 357, 528/361

[56]      References Cited

U.S. PATENT DOCUMENTS 5,386,004   1/1995   Obuchi et al. ......................... 528/354

*Primary Examiner*—Duc Truong
*Attorney, Agent, or Firm*—Birch, Stewart, Kolasch & Birch, LLP

[57]         ABSTRACT

A method for producing a polylactic acid, comprising the steps of carrying out a ring-opening polymerization of lactide to give polylactic acid, adding a compound capable of inactivating a catalyst for ring-opening polymerization of the lactide at the completion of the reaction, and removing unchanged lactide from the polylactic acid product by reducing pressure and/or allowing an inert gas to pass; and a method for forming fiber or film directly from the polylactic acid produced by the invention.

18 Claims, 1 Drawing Sheet

METHOD FOR PRODUCING POLYLACTIC ACID

BACKGROUND OF THE INVENTION

1. Field of the Invention

The present invention relates to a method for producing a solid, thermostable polylactic acid having a high molecular weight. The polylactic acid obtained by the present method can take various shapes such as granular, pelletized, and plate-like forms, and is useful as a bio-compatible and biodegradable polymer.

The present invention also relates to a method for directly spinning said polylactic acid into threads or directly forming films therefrom.

2. Discussion of the Related Art

Polylactic acid is a biologically very safe polymer, and its degradated product, namely lactic acid, is absorbed in vivo. Having above properties, the polylactic acid is useful for medical purposes, including surgical sutures, sustained-release capsules in drug delivery systems, and reinforcing materials for bone fractures. Moreover, it is noted as a degradable plastic, because it is degraded under natural environmental conditions. It is also widely used for mono-axially and biaxially stretched films, fibers, extrusion products, and various other purposes. In the production of the above various formed products, mechanical properties equivalent to those of widely used resins are required for the polylactic acid. In order to achieve the desired mechanical properties, high-molecular weight polylactic acids with little thermal decomposition upon forming are in demand.

Methods for producing polylactic acid are known as follows: In one method, lactic acid is directly subject to dehydration condensation to give a desired product. In another method, a cyclic lactide is first synthesized from lactic acids and then purified by such methods as crystallization, followed by ring-opening polymerization. Various procedures for synthesizing, purifying and polymerizing lactides are disclosed in U.S. Pat. No. 4,057,537, EP-A-261,572, *Polymer Bulletin*, 14, 491–495 (1985), *Makromol. Chem.*, 187, 1611–1628 (1986), and other chemistry literatures. Also, JP-B-56-14688 discloses a method for producing a polylactic acid comprising polymerizing a bimolecular cyclic diester, as an intermediate, using tin octylate or lauryl alcohol as a catalyst. Also, polylactic acid can be produced directly from lactic acid by the methods as described in JP-7-33861, JP-59-96123, and *The Proceedings of The Discussion on Macromolecules*, vol.44, pp.3198–3199.

The polylactic acid thus obtained is pelletized into various forms, such as spheres, cubes, columns, and disrupted pieces, in a size from a rice grain to a bean, to make its handling easy in the forming process.

When the polymerization of lactic acid is carried out at a high temperature, e.g., 180° C., lactide is produced owing to depolymerization. Also, polylactic acid having a high molecular weight of 100,000 to 500,000 has a high melting point of 175° to 200° C. Conventionally, when the final polymer product of the above polylactic acid is taken out of the reactor in a molten state and heated to a temperature higher than its melting point, the polylactic acid undergoes decomposition and coloration. Moreover, a large amount of lactide is generated from the polymer at the above high temperatures presumably owing to the fact that a polymer-lactide equilibrium is shifted toward the lactide side at the above temperatures.

These lactide and decomposition products thereof are liable to sublime during injection molding or spinning of the polylactic acid pellets used as a starting material and undesirably adhere to dice or nozzles, and thereby the operation is hampered. Furthermore, the lactide and the decomposition products lower the glass transition temperature and the melt viscosity of the polymer, resulting in drastic deterioration of moldability and thermal stability. Also, gasified low-molecular components, such as lactide, adversely affect the workplace environment.

When polymerization proceeds to a desired molecular weight in a vertical reactor, the viscosity of the product exceeds 30,000 poise at a reaction temperature of from 120° to 160° C., necessitating strong stirring. Thus, the highly viscous polymer product adheres to the internal surface of the reactor and mixing impellers, thereby causing a decrease in yield, and the necessity of extra steps such as a cleaning step, and coloration of the product.

In an attempt to solve the above problems, JP-A-3-14829 discloses a method where the polymerization product of glycolide or lactide, which is in a molten state, is treated under a reduced pressure. In another attempt, polyglycolide is melted under reduced pressure to remove low-molecular components by distillation [*Kagaku Kogaku Zasshi* 67(2), 362–366(1964)].

The methods above, however, cannot sufficiently remove low-molecular components such as lactide without inactivating the catalyst used for the polymerization, because lactide is in equilibrium with polylactic acid and the equilibrium is catalyzed by the catalyst.

As a method for controlling the catalyst activity for polymerization, JP-B-5-13963 discloses that a phosphoric acid or phosphorous acid compound is added to the reaction mixture at the time when the molecular weight of the polymer reaches 2000 to 6000 and that the polymerization reaction still proceeds. However, this prior art method is directed to the production of polylactic acid by direct polymerization of lactic acid, which is quite different from the method of the present invention directed to the production of polylactic acid by ring-opening polymerization of lactide. Also, the purpose of this prior art method is to slow the rate of the polymerization reaction by adding the phosphoric acid or phosphorous acid compound at the time when the molecular weight of the polymer is still low. Thus, this prior art method is not directed to efficient removal of the low-molecular components, such as lactide, from the polymer by adding phosphoric acid, etc. to inactivate the catalyst completely and hence to stop depolymerization reaction completely.

SUMMARY OF THE INVENTION

An object of the present invention is to provide a method for producing a polylactic acid having a high molecular weight and high thermal stability, which is free from coloration, contains substantially no decomposition products or lactide, and has a desired shape appropriate to a final product.

As a result of intensive research in view of the above object, the present inventors have found that polylactic acid free from coloration and containing substantially no decomposition products can be obtained by removing low-molecular components, mainly lactide, by reducing pressure and/or allowing an inert gas to pass through the reaction mixture during or after polymerization process. Also, the present inventors found that depolymerization of the product can be suppressed by adding a compound capable of lowering the catalyst activity when a weight-average molecular weight of the polylactic acid produced is 50,000 or more. The inventors also found that the compounds capable of suppressing depolymerization of polylactic acid include (a) phosphoric acid or phosphorous acid, or the derivatives thereof; and (b) aluminum compounds. Based upon these findings, the present invention has been completed.

In one embodiment, the present invention relates to a method for producing a polylactic acid, comprising the steps of carrying out a ring-opening polymerization of lactide to give polylactic acid, adding a compound capable of inactivating a catalyst for ring-opening polymerization of the lactide, and removing unchanged lactide from the polylactic acid product by reducing pressure and/or allowing an inert gas to pass through the reaction mixture.

In another embodiment, the present invention relates to a method for forming fiber or film directly from the polylactic acid produced by the method above.

According to the method of the present invention, a formed, particularly pelletized, polylactic acid having a high molecular weight of 200,000 to 500,000 free from coloration and containing substantially no decomposition products can be obtained.

DETAILED DESCRIPTION OF THE INVENTION

Figure 1:
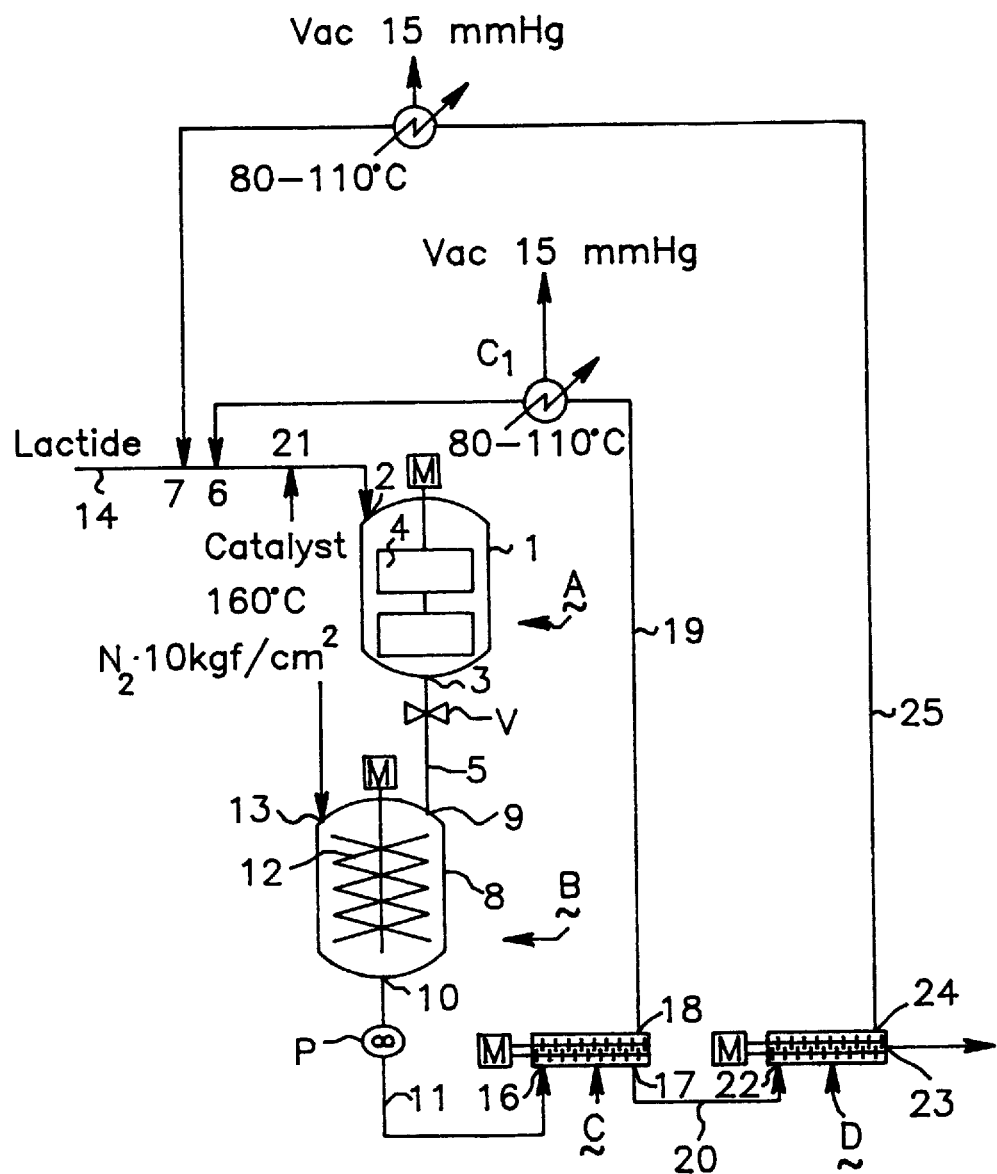
FIG. 1 is a schematic view of an example of the apparatus for carrying out the method of the present invention.

In the present application, the term "unchanged lactide" refers to not only lactide as a starting material monomer but also lactide as a decomposed product of polylactic acid.

The polymerization temperature in the production method of polylactic acids in accordance with the present invention is in the range of 120° to 180° C. Polymerization is preferably carried out in the range of from 140° to 160° C. to prevent racemization, decomposition and coloration of L-lactide. Polylactic acids having a weight-average molecular weight of 50,000 to 300,000 are obtained by polymerization. Polymerization is performed by using one or more vertical reactors and terminated before the polylactic acid becomes too viscous to flow easily. It is preferable to use a plurality of reactors with impellers adapted to different viscosities, since the viscosity of polymer increases as polymerization progresses. Furthermore, in the case of continuous operation, a plurality of reactors are connected in series so as to make the distribution of retention time sharp and extend the area for heat transfer per volume. For example, a reactor with a slanted impeller, a turbine impeller or a full zone impeller is used first to uniformly stir a catalyst when the viscosity is low. Next, a reactor with an impeller adapted to high viscosity, such as a spiral ribbon impeller, is used for stirring. When a plurality of reactors are used, it is not always necessary to make the reaction temperatures of the reactors equal.

With respect to catalysts used in the polymerization of the present invention, a catalyst comprising at least one metal selected from the group consisting of an element of group IA of the periodic table, an element of group IVA of the periodic table, an element of group IVB of the periodic table, and an element of group VB of the periodic table; or a compound thereof is used.

Examples of the catalysts comprising a metal of group IVA or a compound thereof include organotin compounds, such as tin lactate, tin tartrate, tin dicaprylate, tin dilaurate, tin dipalmitate, tin distearate, tin dioleate, tin α-naphthoate, tin β-naphthoate, and tin octylate; and tin powder.

Examples of the catalysts comprising a metal of group IA or a compound thereof include hydroxides of alkali metals, such as sodium hydroxide, potassium hydroxide, and lithium hydroxide, weak acid salts of alkali metals, such as sodium lactate, sodium acetate, sodium carbonate, sodium octylate, sodium stearate, potassium lactate, potassium acetate, potassium carbonate, and potassium octylate, and alkoxides of alkali metals, such as sodium methoxide, potassium methoxide, sodium ethoxide, and potassium ethoxide.

Examples of the catalysts comprising a metal of group IVB include titanium compounds, such as tetrapropyl titanate, and zirconium compounds, such as zirconium isopropoxide.

Examples of the catalyst comprising a metal of group VA include antimony compounds, such as antimony trioxide.

All the above catalysts are conventionally used in polymerization of lactic acids. Among them, catalysts comprising tin or a compound thereof is preferably used in terms of catalyst activity. Also, the molecular weight of the final polymer product can be changed by the amount of catalyst added. Smaller the amount of catalyst used is, higher the molecular weight of the polymer product is, though the reaction rate decreases. Nucleating agents, such as talc, clay, and titanium oxide, may be optionally added.

The lactide used for the method of the present invention may be a D-, L-, or DL-isomer, or a mixture of D- and L-isomers. The above monomer can also be copolymerized with lactones, such as β-propiolactone, δ-valerolactone, ε-caprolactone glycolide, and δ-butyrolactone, dicarboxylic acids, diols, hydroxy carboxylic acids, and aliphatic polyesters. Further, polyhydric alcohols, such as glycerol, may be used to control physical properties.

The conditions for polymerization depend on the catalyst used. When tin octylate is used as the catalyst, polymerization is carried out by heating the reaction mixture normally for 1.0 to 30 hours using the catalyst in an amount of from 0.0001 to 5% by weight, preferably from 0.005 to 0.05% by weight, based on the lactide. The reaction is preferably carried out in an atmosphere or stream of an inert gas, such as a nitrogen gas.

When the polymerization reaction is terminated (for example, when the molecular weight has reached 50,000 or more, preferably when the amount of unchanged lactide has reached 10 to 50 wt %), the unchanged lactide is removed by pressure reduction using a Luwa-type thin-film evaporator or a horizontal single- or dual-axis reactor adapted to highly viscous fluids under a reduced pressure of 1 to 200 mmHg. The melting point of the product rises as the lactide is removed. When the product is retained at a temperature higher than its melting point for an extended period of time, depolymerization occurs and lactide is generated again. Therefore, when a plurality of horizontal reactors are connected in series, it is preferable that the reactant in each reactor should be subjected to reaction at the lowest temperature that allows the reactant to be in the molten state. In addition, when a single extruder is used to remove monomer, it is preferable that the temperatures of the barrels thereof be raised stepwise in the direction from the inlet for the reactant to the outlet for the product. In this case, the temperatures are in the range of 140° to 220° C. When two horizontal reactors are used in a two-stage configuration, the first stage can be provided with a reactor with a spectacle impeller or a reactor with a grid impeller made by Hitachi Ltd., or an N-SCR or HVR made by Mitsubishi Heavy Industries, Ltd., or a Bivolac made by Sumitomo Heavy Industries, Ltd. A conventional extruder can be used for the second stage.

Mainly, unchanged lactide is removed and captured by a cooling condenser, cyclone or the like, and then subjected to melt polymerization again.

The polylactic acid is in equilibrium with lactide in a molten state. When catalytic activity is high, lactide is re-generated, even after it is removed. To remove lactide efficiently, it is therefore necessary to remove lactide at a higher rate than it is re-generated. To facilitate this, the catalytic activity is suppressed by adding the following compounds when the weight-average molecular weight of the product polymer reaches 50,000 or higher: (a) phosphoric acid or phosphorous acid, or the derivatives thereof; and (b) aluminum compounds. These compounds are added in an amount of 0.5 to 20 times by weight of the amount of the catalyst used. Specifically, in case where the compound added is a phosphoric acid compound and the catalyst is a tin compound, the molar ratio of tin compound to phosphoric acid compound is not higher than 0.9, preferably in the range of from 0.05 to 0.8.

Examples of (a) phosphoric acid or phosphorous acid, or the derivatives thereof include phosphoric acid, phosphorous acid, pyrophosphoric acid, polyphosphoric acid, monoethyl polyphosphate, diethyl polyphosphate, triethyl phosphate, triphenyl phosphate, tetraethyl pyrophosphate, tetraphenyl pyrophosphate, trimethyl phosphate, methyl phosphite, triethyl phosphite, triphenyl phosphite, hexamethylamide pyrophosphate, adenosine triphosphate (ATP), tricalcium phosphate, calcium phosphinate, disodium phosphate, monostearic acid phosphate, distearic acid phosphate, tri-n-butyl phosphate, triphenyl phosphite, triphenyl phosphate, diethyl phosphite, dibutyl phosphite, trimethyl phosphite, tributyl phosphite, dipotassium hydrogenphosphate, potassium dihydrogenphosphate, potassium pyrophosphate, calcium phosphinate, calcium pyrophosphate, disodium hydrogenphosphate, sodium dihydrogenphosphate, aluminum phosphate, aluminum dihydrogenphosphate, and bis(3,5-di-t-butyl-4-hydroxybenzylphosphoric acid ethyl) calcium.

Examples of (b) aluminum compounds include aluminum phosphate, aluminum dihydrogenphosphate, aluminum oxide, aluminum lactate, aluminum acetylacetonate, aluminum fluoride, aluminum iodide, aluminum stearate, aluminum tri-n-butoxide, aluminum tri-s-butoxide, aluminum triethoxide, and aluminum triisopropoxide.

Besides the compounds of (a) and (b) above, oxidizing agents such as dibenzoyl peroxide may be used.

The above compounds may be used singly or in combination of two or more kinds.

The polylactic acid obtained by the method explained above may be formed into film or fiber through a die. For example, fibers are spun at a spinning rate of from 500 to 1200 m/min, and drawn at a draw ratio of from 3.0 to 4.5. Also, the obtained polylactic acid may be formed into a desired shape, such as granular and pelletized forms, using a forming machine.

In addition, conventionally known additives, including stabilizers, such as calcium stearate; plasticizers, such as phthalic acid ester; and coloring agents, such as chromium orange and titanium oxide may be added to the polylactic acid.

FIG. 1 is a schematic view showing an apparatus for carrying out the method of the present invention. Referring to FIG. 1, a preferred embodiment of the present invention is hereinafter described in detail.

In the figure, A and B designate vertical reactors mainly used for polymerization, and C and D designate horizontal reactors mainly used for removing unchanged lactide under reduced pressure.

The reactor A comprises a hollow cylindrical reaction tank 1, and the reaction tank 1 is provided with a material supply inlet 2 and a discharge opening 3. To the discharge opening 3, a discharge nozzle 5 is connected. The nozzle 5 is provided with a valve V for controlling polymer to be supplied to the next reactor B. To the material supply inlet 2, a material supply pipe 14 is connected. The pipe 14 is provided with openings 6, 7 connected to recovery pipes for recovering unchanged lactide, and is also provided with an opening 21 connected to a catalyst supply pipe.

A full zone impeller 4 is housed in the reaction tank 1. The drive source (motor) M thereof is installed on the side of the other opening. Around the circumference of the reaction tank 1, a heater (heat medium jacket, not shown) is provided to heat the reaction tank 1. In addition, the temperature inside the reaction tank 1 is monitored by a temperature sensor (not shown).

Like the reactor A, the reactor B comprises a hollow cylindrical reaction tank 8. The reactor B is provided with a supply inlet 9 for supplying polymer from the reaction tank 1 and is also provided with a discharge opening 10. To the discharge opening 10, a connection pipe 11 connected to the next reactor C is connected. The connection pipe 11 is provided with a gear pump P. A spiral ribbon impeller 12 is housed in the reaction tank 8. The drive source (motor) M thereof is installed on the side of the other opening of the reaction tank 1. Furthermore, to the reaction tank 8, a nitrogen gas supply pipe 13 is connected so that nitrogen gas is supplied from a gas cylinder (not shown) to the tank 8 via the pipe. Like the reaction tank 1, the reaction tank 8 is provided with a heater (not shown) and a temperature sensor (not shown).

The horizontal reactor C is provided with a supply inlet 16 for supplying polymer from the reaction tank 8 and is also provided with a discharge opening 17. To the discharge opening 17, a connection pipe 20 connected to the next reactor D is connected. Furthermore, the horizontal reactor C is provided with an opening 18 used to reduce pressure in the tank and connected to a recovery pipe 19 for returning removed unchanged lactide to the reaction tank 1. The recovery pipe 19 is provided with a condenser $C_1$ for liquefying removed unchanged lactide and connected to a vacuum pump (not shown). Moreover, the horizontal reactor C is also provided with a heater and a temperature sensor (these are not shown). M designates a stirring motor.

The horizontal reactor D is provided with a supply inlet 22 for supplying polymer from the horizontal reactor C and also provided with a polymer discharge opening 23. Furthermore, like the horizontal reactor C, the horizontal reactor D is provided with an opening 24 used to reduce pressure in the tank and connected to a recovery pipe 25 for returning removed unchanged lactide to the reaction tank 1. The recovery pipe 25 is provided with a condenser $C_2$ for liquefying removed unchanged lactide and connected to a vacuum pump (not shown). Moreover, the horizontal reactor C is also provided with a heater and a temperature sensor (these are not shown). M designates a stirring motor.

By using the above-mentioned configuration, polylactic acids are produced as described below.

First, L-lactide and a catalyst are supplied to the reaction tank 1 from the material supply inlet 2 via the material supply pipe 14. At this time, the valve V is closed. The material supply inlet 2 is then closed, and a heater (not shown) and the full zone impeller 4 are activated to perform polymerization. At this time, polymerization temperature is monitored and controlled within a predetermined range.

When polymerization progresses and the viscosity of polymer increases after a predetermined time, the valve V is opened, and the polymer is supplied from the nozzle 5 into the reaction tank 8. Polymerization continues in the reaction tank 8 while the spiral ribbon impeller 12 is activated. At this time, the polymerization temperature is monitored and controlled within a predetermined range.

When additional polymerization in the reaction tank 8 has been completed, the polymer is supplied by the gear pump P to the horizontal reactor C and vacuumed from the opening 18. By the vacuuming, unchanged lactide is introduced into the recovery pipe 19, cooled and liquefied by the condenser $C_1$, and then recovered to the reaction tank 1 via the opening 6.

When the operation at the horizontal reactor C has been completed in a predetermined time, the connection pipe 20 is opened to introduce the polymer in the horizontal reactor C into the horizontal reactor D. The same operation as that performed at the horizontal reactor C is also performed at the horizontal reactor D so that unchanged lactide which was not removed at the horizontal reactor C is recovered via the opening 7.

When the operation at the horizontal reactor D has been completed, the polymer (polylactic acid) is discharged from the opening 23 in the form of a thread, film or strand.

In the above-mentioned operations, the temperatures in the reaction tanks 1, 8 and the horizontal reactor C are set at 160° C. for example, the temperature in the horizontal reactor D is set at 200° C. for example, and the temperatures of the condensers $C_1$ and $C_2$ are set at 80° to 110° C. for example. In addition, when a phosphorus compound is added, the addition is performed before pressure reduction, namely, at the preceding stage of the horizontal reactors C and D by using the connection pipe 11 provided with an opening for phosphorous compound addition.

Polylactic acid is labile at high temperatures, which makes it impossible to reduce viscosity by increasing temperature. In the present invention, lactide, i.e., the starting monomer, itself works as a solvent and is recycled during the polymerization process to reduce the viscosity of the polylactic acid.

In the reaction system where one or more vertical reactors are connected in series with one or more horizontal reactors, the polymer product can be smoothly taken out of the vertical reactor, and continuous operations can be achieved. Also, since a polymer free from unchanged lactide can be obtained by the method of the present invention, the extraction step to remove unchanged lactide from the polymer product can be omitted.

EXAMPLES

The present invention will be further described by means of the following working examples, without intending to restrict the scope of the present invention thereto.

GPC and DSC in each of Examples were measured under the following conditions:
GPC
  Detector: RID-6A
  Pump: LC-9A
  Column oven: CTO-6A
  Columns: Connecting in series: SHIM PACK GPC-801C, GPC-804C, GPC-806C, and GPC-8025C.

Here, the detector, the pump, the column oven, and the columns are all manufactured by Shimadzu Corporation.
  Analysis conditions:
    Solvent: Chloroform
    Flow rate: 1 ml/min
    Amount of sample: 20 µl (dissolving concentration of 0.5% by weight in chloroform)
    Column temp.: 40° C.
DSC
  DSC-50 (manufactured by Shimadzu Corporation)
  Temperature raising velocity: 10° C./min
  Amount of sample: 6 to 7 mg Example 1-1

A homemade lactide of 50 kg was supplied to a 50 L vertical reactor (reactor A) with a full zone impeller (trade name: Full zone impeller, manufactured by Shinko Pantec). After dissolution at 120° C., 25 g (500 ppm) of tin octylate was added and subjected to reaction at 160° C. for 5 hours. At this time, unchanged lactide amounted to 70%. The contents were sent in the form of liquid to a 50 L vertical reactor (reactor B) with a spiral ribbon impeller (manufactured by Shinko Pantec). The lactide was further subjected to reaction for additional 5 hours. At this time, unchanged lactide amounted to 50%.

The contents were introduced at a rate of 10 kg/hour into a horizontal dual-axis reactor (N-SCR) (reactor C) having an internal capacity of 6.5 L (manufactured by Mitsubishi Heavy Industries, Ltd.). The operation temperature of the reactor was set at 160° C., and vacuuming was performed from a vent (opening) under a reduced pressure of 15 mmHg. The concentration of the unchanged lactide at the outlet was 5%. The removed lactide was liquefied by condenser having a cooling area of 3 m² (manufactured by Karbate), and returned to the reactor A.

Next, the lactide was introduced into an extruder having 8 barrels (reactor D) made by Kurimoto Ltd., and phosphorous acid was added at a rate of 10 mg/minute from the third barrel having been set at 200° C. Vacuuming was performed under a reduced pressure of 15 mmHg from the vent (opening) of the seventh barrel. The removed lactide was captured by a condenser having a cooling area of 1 m², and returned to the reactor A.

The polymer was discharged from a spinning nozzle having five holes measuring 0.4 mm in diameter at a discharging speed of 1.5 g/min per hole. The thread thinning completion point was 30 cm from the spinning nozzle. The polymer is then introduced into a cooling pipe. The fiber thus obtained was further subjected to drawing and heating treatment, and the strength and the tensile elastic modulus of the fiber were evaluated; they were 9 g/d and 150 g/d or more, respectively. The unchanged lactide contained was about 100 ppm or less, and the molecular weight of the polymer product was 150,000.

Example 1-2

A homemade lactide of 50 kg was supplied to a 50 L vertical reactor (reactor A) with a full zone impeller (trade name: Full zone impeller). After dissolution at 120° C., 0.5 g (10 ppm) of tin octylate was added and subjected to reaction at 160° C. for 5 hours. At this time, unchanged lactide amounted to 80%. The contents were sent in the form of liquid to a 50 L vertical reactor (reactor B) with a spiral ribbon impeller (manufactured by Shinko Pantec). The lactide was further subjected to reaction for additional 5 hours. At this time, unchanged lactide amounted to 60%.

The contents were introduced at a rate of 10 kg/hour into a horizontal dual-axis reactor (N-SCR) (reactor C) having an internal capacity of 6.5 L (manufactured by Mitsubishi Heavy Industries, Ltd.). The operation temperature of the reactor was set at 160° C., and vacuuming was performed from a vent (opening) under a reduced pressure of 15 mmHg. The concentration of the unchanged lactide at the outlet was 7%. The removed lactide was liquefied by condenser having a cooling area of 3 m$^2$ (manufactured by Karbate), and returned to the reactor A.

Next, the lactide was introduced into an extruder having 8 barrels (reactor D) made by Kurimoto Ltd., and vacuuming was performed under a reduced pressure of 15 mmHg from the vent (opening) of the seventh barrel having been set at 200° C. The removed lactide was captured by a condenser having a cooling area of 1 m$^2$, and returned to the reactor A.

The polymer was discharged from a die having three holes measuring 8 mm in diameter. The polymer is then cooled in a water vessel, and cut by a strand cutter to obtain pellets. Analysis of the pelletized polymer revealed that weight-average molecular weight of the polymer is 155,000; the unchanged lactide contained was about 60 ppm, glass transition temperature was 61° C.

Example 1-3

Procedures similar to those in Example 1 were followed except for the followings. The rate at which the reactant was introduced into reactor C was adjusted to 6.5 kg/hour, instead of 10 kg/hour. Also, a gear pump was provided at the outlet of the reactor D, and a spinning nozzle having 48 holes measuring 0.25 mm in diameter was provided downstream the pump, from which the polymer was discharged. The polymer was then rolled around a bobbin at a first and final take-up speed of 800 m/min and 3600 m/min, respectively, at a hot plate temperature of 140° C. to give a stretched thread. The tensile strength of the thread was 4.5 g/d and the elongation at break was 26.2%.

Example 2-1

In a 1000-ml flask equipped with a stirrer and a thermometer, 500 g of L-lactide was placed. The lactide was melted at 150° C. while stirring in a nitrogen atmosphere, to which 0.05 g of tin octylate was added. One hour later, 0.02 g of phosphoric acid was added to the reaction mixture, the molar ratio of tin compound to phosphoric acid compound being 0.6, and stirred for 15 minutes. The contents of the flask was transferred to a horizontal twin-screw kneader, in which unchanged lactide was removed at a temperature of 190° C. under a reduced pressure of 10 mmHg. Ten minutes later, pelletized polylactic acid was collected. The molecular weight of the polylactic acid determined by GPC was 183,000.

In a 10-ml test tube, about one g of the polylactic acid obtained above was placed. The internal air of the test tube was replaced with an N$_2$ gas, and the test tube was sealed. Thereafter, a heat decomposition test was carried out by keeping the test tube at 190° C. for 30 minutes. The results are shown in Table 2-1.

For comparison, the same procedures for producing polylactic acid as those above were followed without addition of phosphoric acid. The polylactic acid obtained has a molecular weight of 148,000. This polylactic acid was also subjected to a heat decomposition test. The results of the test are shown in Table 2-1.

As shown in Table 2-1, it was found that polylactic acid obtained by the method of the present invention has a higher thermal stability than that obtained by the comparison experiment.

Example 2-2

In a 1000-ml flask equipped with a stirrer and a thermometer, 500 g of L-lactide was placed. The lactide was melted at 140° C. while stirring in a nitrogen atmosphere, to which 0.1 g of tin octylate was added. One hour later, 0.2 g of pyrophosphoric acid was added to the reaction mixture, the molar ratio of tin compound to phosphorus compound being 0.1, and stirred for 15 minutes. The contents of the flask was transferred to a horizontal twin-screw kneader, in which unchanged lactide was removed at a temperature of 190° C. under a reduced pressure of 10 mmHg. Ten minutes later, pelletized polylactic acid was collected. The molecular weight of the polylactic acid determined by GPC was 162,000.

In a 10-ml test tube, about one g of the polylactic acid obtained above was placed. The internal air of the test tube was replaced with an N$_2$ gas and the test tube was sealed. Thereafter, a heat decomposition test was carried out by keeping the test tube at 190° C. for 30 minutes. The results are shown in Table 2-1.

For comparison, the same procedures as those above were followed without addition of pyrophosphoric acid. The polylactic acid obtained has a molecular weight of 125,000. This polylactic acid was also subjected to a heat decomposition test. The results of the test are shown in Table 2-1.

As shown in Table 2-1, it was found that polylactic acid obtained by the method of the present invention has a higher thermal stability than that obtained by the comparison experiment.

Example 2-3

In a 1000-ml flask equipped with a stirrer and a thermometer, 500 g of L-lactide was placed. The lactide was melted at 150° C. while stirring in a nitrogen atmosphere, to which 0.05 g of tin octylate was added. One hour later, 0.013 g of phosphoric acid was added to the reaction mixture, the molar ratio of tin compound to phosphorus compound being 0.9, and stirred for 15 minutes. The contents of the flask was transferred to a horizontal twin-screw kneader, in which unchanged lactide was removed at a temperature of 190° C. under a reduced pressure of 10 mmHg. Ten minutes later, pelletized polylactic acid was collected. The molecular weight of the polylactic acid determined by GPC was 168,000.

In a 10-ml test tube, about one g of the polylactic acid obtained above was placed. The internal air of the test tube was replaced with an N$_2$ gas and the test tube was sealed. Thereafter, a heat decomposition test was carried out by keeping the test tube at 190° C. for 30 minutes. The results are shown in Table 2-1.

For comparison, the same procedures as those above were followed without addition of phosphoric acid. The polylactic acid obtained has a molecular weight of 148,000. This polylactic acid was also subjected to a heat decomposition test. The results of the test are shown in Table 2-1.

As shown in Table 2-1, when the molar ratio of tin to phosphorus compound exceeds 0.9, the molecular weight of the product is significantly decreased owing to heat decomposition and the object of the present invention, therefore, cannot be achieved.

TABLE 2-1

|  | MW before heat decomposition | MW after heat decomposition | MW lowering rate (%) |
|---|---|---|---|
| Example 2-1 | 183,000 | 175,000 | 4.37 |
| Comparative Example 2-1 | 148,000 | 82,000 | 44.59 |
| Example 2-2 | 162,000 | 160,000 | 1.23 |
| Comparative Example 2-2 | 125,000 | 48,000 | 61.60 |
| Example 2-3 | 168,000 | 122,000 | 27.38 |
| Comparative Example 2-3 | 148,000 | 82,000 | 44.59 |

Example 3-1

In a 1000-ml flask equipped with a stirrer and a thermometer, 500 g of L-lactide was placed. The lactide was melted at 160° C. while stirring in a nitrogen atmosphere, to which 0.05 g of tin octylate was added. Two hours later, 0.05 g of aluminum oxide (1.0 time the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 180,000.

In a 10-ml test tube with a stopper, about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 3-1.

Example 3-2

In a 1000-ml flask equipped with a stirrer and a thermometer, 500 g of L-lactide was placed. The lactide was melted at 160° C. while stirring in a nitrogen atmosphere, to which 0.05 g of tin octylate was added. Two hours later, 0.25 g of aluminum phosphate (5 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 185,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 3-1.

Example 3-3

In a 1000-ml flask equipped with a stirrer and a thermometer, 500 g of L-lactide was placed. The lactide was melted at 160° C. while stirring in a nitrogen atmosphere, to which 0.05 g of tin octylate was added. Two hours later, 0.5 g of aluminum dihydrogenphosphate (10 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 180,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 3-1.

Example 3-4

In a 1000-ml flask equipped with a stirrer and a thermometer, 500 g of L-lactide was placed. The lactide was melted at 160° C. while stirring in a nitrogen atmosphere, to which 0.05 g of tin octylate was added. Two hours later, 0.025 g of aluminum dihydrogenphosphate (0.5 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 175,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 3-1.

Example 3-5

In a 1000-ml flask equipped with a stirrer and a thermometer, 500 g of L-lactide was placed. The lactide was melted at 160° C. while stirring in a nitrogen atmosphere, to which 0.05 g of tin octylate was added. Two hours later, 1.0 g of aluminum dihydrogenphosphate (20.0 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 170,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 3-1.

Example 3-6

In a 1000-ml flask equipped with a stirrer and a thermometer, 500 g of L-lactide was placed. The lactide was melted at 160° C. while stirring in a nitrogen atmosphere, to which 0.05 g of tin octylate was added. Two hours later, 0.01 g of aluminum dihydrogenphosphate (0.2 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 160,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 3-1.

Example 3-7

In a 1000-ml flask equipped with a stirrer and a thermometer, 500 g of L-lactide was placed. The lactide was melted at 160° C. while stirring in a nitrogen atmosphere, to which 0.05 g of tin octylate was added. Two hours later, 1.2 g of aluminum dihydrogenphosphate (24.0 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 150,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 3-1.

Comparative Example 3-1

For comparison, the same procedures as the above examples were followed without addition of aluminum compound. The polylactic acid thus obtained had a molecular weight of 145,000. This polylactic acid was also subjected to the same heat decomposition test. The results of the test are shown in Table 3-1.

As shown in Table 3-1, when polylactic acid was prepared without adding aluminum compound, the molecular weight of the product after heat decomposition was significantly lowered, indicating that the product polymer is not thermostable.

pressure of 10 mmHg. Ten minutes later, pelletized polylactic acid was collected. The molecular weight of the polylactic acid determined by GPC was 185,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 4-1.

Example 4-2

In a 1000-ml flask equipped with a stirrer and a thermometer, 500 g of L-lactide was placed. The lactide was melted at 160° C. while stirring in a nitrogen atmosphere, to which 0.05 g of tin octylate was added. Two hours later, 0.4 g of distearic acid phosphate (8.0 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 186,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 4-1.

Example 4-3

In a 1000-ml flask equipped with a stirrer and a thermometer, 500 g of L-lactide was placed. The lactide was melted at 160° C. while stirring in a nitrogen atmosphere, to which 0.05 g of tin octylate was added. Two hours later, 0.7 g of a mixture of monostearic acid phosphate and distearic acid phosphate (Adekastab AX-71™) (14.0 times the weight of tin octylate) was added to the reaction mixture, and stirred for 15 minutes. The contents of the flask was transferred to

TABLE 3-1

| | Ratio of inactivating compound to catalyst | MW before heat decomposition | MW after heat decomposition | MW lowering rate (%) | Coloration |
|---|---|---|---|---|---|
| Example 3-1 | 1.0 | 180000 | 175000 | 2.8 | No |
| Example 3-2 | 5.0 | 185000 | 180000 | 2.7 | No |
| Example 3-3 | 10 | 180000 | 175000 | 2.8 | No |
| Example 3-4 | 0.5 | 175000 | 165000 | 5.7 | No |
| Example 3-5 | 20.0 | 170000 | 160000 | 5.9 | No |
| Example 3-6 | 0.2 | 160000 | 130000 | 18.8 | No |
| Example 3-7 | 24 | 150000 | 120000 | 20.0 | Yes (turbid) |
| Comparative Example 3-1 | — | 145000 | 80000 | 44.8 | No |

Example 4-1

In a 1000-ml flask equipped with a stirrer and a thermometer, 500 g of L-lactide was placed. The lactide was melted at 160° C. while stirring in a nitrogen atmosphere, to which 0.05 g of tin octylate was added. Two hours later, 0.2 g of monostearic acid phosphate (4.0 times the weight of tin octylate) was added to the reaction mixture, and stirred for 15 minutes. The contents of the flask was transferred to a horizontal twin-screw kneader, in which unchanged lactide was removed at a temperature of 180° C. under a reduced a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 180,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 4-1.

Example 4-4

In a 1000-ml flask equipped with a stirrer and a thermometer, 500 g of L-lactide was placed. The lactide was melted at 160° C. while stirring in a nitrogen atmosphere, to which 0.05 g of tin octylate was added. Two hours later, 0.025 g of Adekastab AX-71™ (0.5 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 172,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 4-1.

Example 4-5

In a 1000-ml flask equipped with a stirrer and a thermometer, 500 g of L-lactide was placed. The lactide was melted at 160° C. while stirring in a nitrogen atmosphere, to which 0.05 g of tin octylate was added. Two hours later, 0.025 g of Adekastab AX-71™ (20 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 170,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 4-1.

Example 4-6

In a 1000-ml flask equipped with a stirrer and a thermometer, 500 g of L-lactide was placed. The lactide was melted at 160° C. while stirring in a nitrogen atmosphere, to which 0.05 g of tin octylate was added. Two hours later, 0.01 g of Adekastab AX-71™ (0.2 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 165,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 4-1.

Example 4-7

In a 1000-ml flask equipped with a stirrer and a thermometer, 500 g of L-lactide was placed. The lactide was melted at 160° C. while stirring in a nitrogen atmosphere, to which 0.05 g of tin octylate was added.

Two hours later, 1.2 g of Adekastab AX-71™ (24 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 162,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 4-1.

Comparative Example 4-1

For comparison, the same procedures as the above examples were followed without addition of phosphoric acid ester. The polylactic acid obtained had a molecular weight of 150,000. This polylactic acid was also subjected to the same heat decomposition test. The results of the test are shown in Table 4-1.

As shown in Table 4-1, when polylactic acid was prepared without adding phosphoric acid ester, the molecular weight of the product after heat decomposition was significantly lowered, indicating that the product polymer is not thermostable.

TABLE 4-1

|  | Ratio of inactivating compound to catalyst | MW before heat decomposition | MW after heat decomposition | MW lowering rate (%) | Coloration |
| --- | --- | --- | --- | --- | --- |
| Example 4-1 | 4.0 | 185000 | 182000 | 1.6 | No |
| Example 4-2 | 8.0 | 186000 | 184000 | 1.1 | No |
| Example 4-3 | 14.0 | 180000 | 178000 | 1.1 | No |
| Example 4-4 | 0.5 | 172000 | 164000 | 4.7 | No |
| Example 4-5 | 20.0 | 170000 | 164000 | 3.5 | No |
| Example 4-6 | 0.2 | 165000 | 130000 | 21.2 | No |
| Example 4-7 | 24.0 | 162000 | 130000 | 19.8 | Yes (turbid) |
| Comparative Example 4-1 | — | 150000 | 90000 | 40.0 | No | melted at 160° C. while stirring in a nitrogen atmosphere, to

Example 5-1

In a 1000-ml flask equipped with a stirrer and a thermometer, 500 g of L-lactide was placed. The lactide was melted at 160° C. while stirring in a nitrogen atmosphere, to which 0.05 g of tin octylate was added. One hour later, 0.4 g (8.0 times the weight of tin octylate) of a mixture of calcium salt of ethyl bis(3-5-di-t-butyl-4-hydroxybenzyl phosphoric acid ester and polyethylene wax (1:1, IRGANOX 1425 WL) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 165,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 5-1.

Example 5-2

In a 1000-ml flask equipped with a stirrer and a thermometer, 500 g of L-lactide was placed. The lactide was melted at 160° C. while stirring in a nitrogen atmosphere, to which 0.05 g of tin octylate was added. One hour later, 0.1 g of potassium pyrophosphate (2.0 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 160,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 5-1.

Example 5-3

In a 1000-ml flask equipped with a stirrer and a thermometer, 500 g of L-lactide was placed. The lactide was melted at 160° C. while stirring in a nitrogen atmosphere, to which 0.05 g of tin octylate was added. One hour later, 0.5 g of sodium dihydrogenphosphate (10.0 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 170,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 5-1.

Example 5-4

In a 1000-ml flask equipped with a stirrer and a thermometer, 500 g of L-lactide was placed. The lactide was melted at 160° C. while stirring in a nitrogen atmosphere, to which 0.05 g of tin octylate was added. One hour later, 0.025 g of sodium dihydrogenphosphate (0.5 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 155,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 5-1.

Example 5-5

In a 1000-ml flask equipped with a stirrer and a thermometer, 500 g of L-lactide was placed. The lactide was melted at 160° C. while stirring in a nitrogen atmosphere, to which 0.05 g of tin octylate was added. One hours later, 1.0 g of sodium dihydrogenphosphate (20.0 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 155,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 5-1.

Example 5-6

In a 1000-ml flask equipped with a stirrer and a thermometer, 500 g of L-lactide was placed. The lactide was melted at 160° C. while stirring in a nitrogen atmosphere, to which 0.05 g of tin octylate was added. One hour later, 0.01 g of potassium pyrophosphate (0.2 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 140,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 5-1.

Example 5-7

In a 1000-ml flask equipped with a stirrer and a thermometer, 500 g of L-lactide was placed. The lactide was melted at 160° C. while stirring in a nitrogen atmosphere, to which 0.05 g of tin octylate was added. One hour later, 1.2 g of potassium pyrophosphate (24 times the weight of tin octylate) was added to the reaction mixture, and stirred for 15 minutes. The contents of the flask was transferred to a horizontal twin-screw kneader, in which unchanged lactide was removed at a temperature of 180° C. under a reduced pressure of 10 mmHg. Ten minutes later, pelletized polylactic acid was collected. The molecular weight of the polylactic acid determined by GPC was 150,000.

In a 10-ml test tube with a stopper about one g of the polylactic acid obtained above was placed. The internal air of the test tube was replaced with an $N_2$ gas. Thereafter, a heat decomposition test was carried out by keeping the test tube at 190° C. for 30 minutes. The results are shown in Table 5-1.

Comparative Example 5-1

For comparison, the same procedures as the above examples were followed without addition of phosphoric acid metal salt. The polylactic acid obtained had a molecular weight of 145,000. This polylactic acid was also subjected to the same heat decomposition test. The results of the test are shown in Table 5-1.

As shown in Table 5-1, when polylactic acid was prepared without adding phosphoric acid ester, the molecular weight of the product after heat decomposition was significantly lowered, indicating that the product polymer is not thermostable.

TABLE 5-1

|  | Ratio of inactivating compound to catalyst | MW before heat decomposition | MW after heat decomposition | MW lowering rate (%) | Coloration |
| --- | --- | --- | --- | --- | --- |
| Example 5-1 | 8.0 | 165000 | 155000 | 6.1 | No |
| Example 5-2 | 2.0 | 160000 | 150000 | 6.3 | No |
| Example 5-3 | 10.0 | 170000 | 165000 | 3.1 | No |
| Example 5-4 | 0.5 | 155000 | 140000 | 2.9 | No |
| Example 5-5 | 20.0 | 155000 | 145000 | 6.5 | No |
| Example 5-6 | 0.2 | 140000 | 110000 | 21.4 | No |
| Example 5-7 | 24.0 | 150000 | 125000 | 16.7 | Yes (turbid) |
| Comparative Example 5-1 | — | 130000 | 80000 | 38.5 | No |

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing a polylactic acid, comprising the steps of:
   carrying out a ring-opening polymerization of lactide in the presence of a catalyst for ring-opening polymerization of the lactide to give polylactic acid;
   adding a compound capable of inactivating the catalyst to the resulting reaction mixture; and
   reducing pressure in a reactor containing the reaction mixture and/or allowing an inert gas to pass through the reactor to remove unchanged lactide from the polylactic acid.

2. The method according to claim 1, wherein the compound capable of inactivating the catalyst is added when a weight-average molecular weight of the polylactic acid produced is 50,000 or more.

3. The method according to claim 1, wherein the unchanged lactide is removed from the polylactic acid product which is in a molten or solid state.

4. The method according to claim 1, wherein the unchanged lactide is removed after the completion of the ring-opening polymerization.

5. The method according to claim 1, wherein the unchanged lactide is removed when amount of the unchanged lactide becomes 10 to 50% by weight.

6. The method according to claim 1, wherein the compound capable of inactivating the catalyst used for ring-opening polymerization is selected from the group consisting of (a) phosphoric acid or phosphorous acid, or the derivatives thereof; and (b) aluminum compounds.

7. The method according to claim 5, wherein the compound capable of inactivating the catalyst is added in an amount of 0.5 to 20 times by weight of the amount of a catalyst used for the ring-opening polymerization.

8. The method according to claim 5, wherein a tin compound is used as the catalyst and a compound selected from (a) of claim 5 is used as the compound capable of inactivating the catalyst for ring-opening polymerization, the ratio of the catalyst to the compound selected from (a) of claim 5 being not less than 0.03 and not more than 0.9 with a proviso that tin is divalent and phosphorus is tetravalent.

9. The method according to claim 1, wherein the unchanged lactide removed is recycled.

10. The method according to claim 1, wherein the ring-opening polymerization of lactide is carried out in a vertical system comprising one or more vertical reactors connected in series and wherein the unchanged lactide is removed in a horizontal system comprising one or more horizontal reactors connected in series, said vertical system being connected to said horizontal system in series.

11. The method according to claim 1, wherein the polylactic acid is a copolymer with other monomers.

12. The method according to claim 1, wherein the polylactic acid is blended with other resins.

13. The method according to claim 8, wherein the unchanged lactide removed in the horizontal system is returned to the vertical system via a recovery line which connects the horizontal system with the vertical system so as to be used as a starting material for the ring-opening polymerization.

14. A method for forming fiber or film directly from the polylactic acid produced by the method of claim 1.

15. The method of claim 1 wherein polymerization temperature is 120° to 180° C.

16. The method of claim 1 wherein the catalyst is selected from the group consisting of an element of group IA, an element of Group IVA, an element of group IVB, and an element of group VB, of the periodic table, and compounds thereof.

17. The method of claim 8, wherein said tin compound is selected from the group consisting of tin lactate, tin tartrate, tin dicaprylate, tin dilaurate, tin dipalmitate, tin distearate, tin dioleate, tin α-naphthoate, tin β-naphthoate, and tin octylate.

18. The method of claim 6, wherein in said compound capable of inactivating the catalyst is selected from the group consisting of pyrophosphoric acid, polyphosphoric acid, monoethyl polyphosphate, diethyl polyphosphate, triethyl phosphate, triphenyl phosphate, tetraethyl pyrophosphate, tetraphenyl pyrophosphate, trimethyl phosphate, methyl phosphite, triethyl phosphite, triphenyl phosphite, hexamethylamide pyrophosphate, adenosine triphosphate (ATP), tricalcium phosphate, calcium phosphinate, disodium phosphate, monostearic acid phosphate, distearic acid phosphate, tri-n-butyl phosphate, triphenyl phosphite, triphenyl phosphate, diethyl phosphite, dibutyl phosphite, trimethyl phosphite, tributyl phosphite, dipotassium hydrogenphosphate, potassium dihydrogenphosphate, potassium pyrophosphate, calcium phosphinate, calcium pyrophosphate, disodium hydrogenphosphate, sodium dihydrogenphosphate, aluminum phosphate, aluminum dihydrogenphosphate, bis(3,5-di-t-butyl-4-hydroxybenzylphosphoric acid ethyl) calcium, aluminum oxide, aluminum lactate, aluminum acetylacetonate, aluminum fluoride, aluminum iodide, aluminum stearate, aluminum tri-n-butoxide, aluminum tri-s-butoxide, aluminum triethoxide, and aluminum triisopropoxide.

\* \* \* \* \*